United States Patent [19]

Schiessl

[11] 4,306,986

[45] Dec. 22, 1981

[54] SELECTED POLY(OXYALKYLATED) PYRAZOLES AND THEIR USE AS CORROSION INHIBITORS

[75] Inventor: Henry W. Schiessl, Northford, Conn.

[73] Assignee: Olin Corporation, New Haven, Conn.

[21] Appl. No.: 202,966

[22] Filed: Nov. 3, 1980

[51] Int. Cl.³ .................... C07D 231/12; C09K 15/30; C23F 11/04; C23G 1/06
[52] U.S. Cl. ........................................ 252/77; 252/68; 252/136; 252/148; 252/390; 422/12; 422/16; 548/373
[58] Field of Search ................... 252/68, 77, 136, 148, 252/390, 394; 422/12, 16; 548/373

[56] References Cited

U.S. PATENT DOCUMENTS 2,160,293  5/1939  Shoemaker ..................... 548/373 X
2,618,608 11/1952  Schaeffer ....................... 252/390 X
3,553,101  1/1971  Foroulis ......................... 252/390 X
3,778,376 12/1973  Herber ................................. 252/78

OTHER PUBLICATIONS

Kirk-Othmer, Encyclopedia of Chemical Technology, vol. 16, pp. 762-779 (1968).

Primary Examiner—Dennis L. Albrecht
Attorney, Agent, or Firm—William A. Simons; Thomas P. O'Day

[57] ABSTRACT

Disclosed are selected poly(oxyalkylated) pyrazoles of the formula:

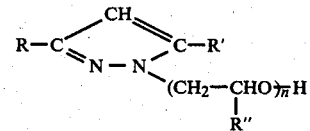

wherein R and R' are independently selected from lower alkyl groups having 1 to 4 carbon atoms; each R" is individually selected from hydrogen and methyl; and n is from 2 to about 20. These compounds are shown to be effective corrosion inhibitors in corrosive liquids such as acids, antifreezes and hydraulic fluids.

27 Claims, No Drawings

SELECTED POLY(OXYALKYLATED) PYRAZOLES AND THEIR USE AS CORROSION INHIBITORS

BACKGROUND OF THE INVENTION

1. Field of the Invention

This invention relates to selected poly(oxyalkylated) pyrazoles and their use as corrosion inhibitors.

2. Description of the Prior Art

The prior art has disclosed a wide variety of chemical compounds which effectively reduce the corrosive properties of liquids such as antifreezes, acid treating baths and hydraulic fluids. These inhibitors are generally added to the corrosive liquids to protect the metals in contact with these liquids. Alternatively, such inhibitors may be applied first to the metal surface, either as is, or as a solution in some carrier liquid or paste.

While many of these known inhibitors have been used successfully for many years, stricter toxicological and other environmental standards are restricting the use of some of the compounds (e.g., chromates and dichromates). Accordingly, there is a need in the art to develop new and effective corrosion inhibitors which do not pose these environmental problems.

BRIEF SUMMARY OF THE INVENTION

The present invention is directed to, as compositions of matter, selected poly(oxyalkylated) pyrazoles of the formula (I):

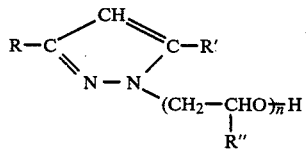

wherein R and R' are independently selected from lower alkyl groups having 1 to 4 carbon atoms; each R" is individually selected from hydrogen and methyl; and n is from 2 to about 20. The present invention is also directed toward the use of these compounds as corrosion inhibitors.

DETAILED DESCRIPTION

The poly(oxyalkylated) pyrazole compounds of the present invention may be prepared by reacting the corresponding 3,5-di(lower alkyl) pyrazole with two or more moles of either ethylene oxide or propylene oxide to produce the desired poly(oxyalkylated) pyrazole. This general reaction is illustrated by the following Equation (A) wherein 3,5-dimethylpyrazole is reacted with 10 moles of ethylene oxide to produce the desired 3,5-dimethylpyrazole.10 ethylene oxide adduct product:

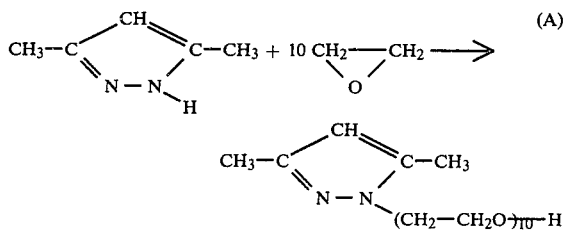

The 3,5-di(lower alkyl) pyrazole reactants are commonly made by reacting hydrazine with a 1,3-diketone such as acetylacetone. The general synthesis of these compounds may be found in an article entitled "Synthesis of Pyrazoles" by T. L. Jacobs, which is in *Heterocyclic Compounds*, Vol. 5, Chapter 2, Editor—R. C. Elderfield, John Wiley & Sons, Inc., New York, 1957. A preferred compound of this class is 3,5-dimethylpyrazole. Note that the 3- and 5-position substituents on the pyrazole ring do not necessarily have to be the same lower alkyl group.

It should also be noted that the number of EO or PO units per ring unit is not the same for ever ring, but rather is statistically distributed. Thus, n in Formula (I) represents the average number of EO or PO units per ring and that the actual number on any given ring may be less or greater than n. That is, when n=10, it is meant that ten moles of EO or PO have been reacted per mole of the pyrazole. Preferably, it is desired to employ from about 5 to about 20 moles of EO or PO per one mole of the pyrazole. More preferably, it is desired to use from about 5 to about 10 moles per mole of the pyrazole.

The ethylene oxide (EO) and propylene oxide (PO) reactants are commercially available chemicals which may be obtained from many sources. Mixtures of EO and PO may also be employed as reactants, either added sequentially or mixed together.

Any conventional reaction conditions designed to produce these poly(oxyalkylated) pyrazoles may be employed in the synthesis of the present compounds and the present invention is not intended to be limited to any particular reaction conditions. Advantageously and preferably, the present compounds may be made according to the reaction illustrated by Equation (A) in the presence of an inert solvent such as toluene and an alkaline catalyst like powdered potassium hydroxide. However, the use of a solvent and a catalyst is only desirable, and not necessary. The reaction temperature and time will both depend upon many factors including the specific reactants and apparatus employed. In most situations, reaction temperatures from about 50° C. to about 200° C., preferably from about 100° C. to about 150° C., may be employed. Reaction times from about 30 minutes to about 600 minutes may be employed. The reaction may preferably be carried out under pressure from about 10 to about 100 psig or more, if desired. The desired adduct product may be recovered from the reaction mixture by any conventional means, for example, evaporation of the solvent, filtration, extraction, recrystallization or the like.

It should be noted that while the reaction illustrated by Equation (A) is the preferred method for preparing the compounds of the present invention, other synthetic methods may also be employed.

Also, in accordance with the present invention, it has been found that the compounds of Formula (I), above, may be utilized as effective corrosion inhibitors. In practicing the process of the present invention, metal surfaces are contacted with an effective corrosion-inhibiting amount of one or more of these compounds. "Metal surfaces" which may be protected by the corrosion-inhibition properties of the compounds of the present invention include ferrous and non-ferrous metals such as cast iron, steel, brass, copper, solder, aluminium and other materials commonly used with corrosive liquids. It is understood that the term "effecive corrosion-inhibiting amount" as used in the specification and claims herein is intended to include any amount that will prevent or control the corrosion on said metal surfaces. Of course, this amount may be constantly changing because of the possible variations in many parameters. Some of these parameters may include the specific corrosive material present; the specific compound used; the specific metal to be protected against corrosion; the salt and oxygen content in the system; the geometry and capacity of the system to be protected against corrosion; flow velocity of the corrosive material; temperature and the like.

One preferred use for the corrosion inhibitors of the present invention is in antifreeze compositions comprising a water-soluble liquid alcohol freezing point depressant. For example, an antifreeze composition containing an effective corrosion-inhibiting amount of one or more of the compounds of Formula (I) may be used in heat exchange systems such as the general antifreeze system for automotive engines. The antifreeze compositions of this invention may contain, besides the freezing point depressant and the corrosion inhibitor, other conventional additives such as dyes, antifoam agents and the like.

The freezing point depressants of the present invention include any of the water miscible liquid alcohols such as monohydroxy lower alkyl alcohols and the liquid polyhydroxy alcohols such as the alkylene and dialkylene glycols. Specific examples of the alcohol contemplated herein are methanol, ethanol, propanol, isopropanol, butanol, ethylene glycol, diethylene glycol, propylene glycol, butylene glycol, and mixtures thereof. A preferred glycol is ethylene glycol, which as sold commercially often contains a small amount, up to 10% by weight, of diethylene glycol. The term ethylene glycol as used herein is intended to include either the pure or commerical compound. This is also true of the other freezing point depressant alcohols contemplated herein. Generally, the freezing point depressant (or depressants) is mixed with water to make aqueous solutions containing from about 10% to about 90% by weight of the depressant.

While the effective amount of corrosion inhibitors in antifreeze solutions may vary on account of the many factors listed above, the general effective range is from about 0.001% to about 5% by weight of the total amount of freezing point depressant in the aqueous solution which is in contact with metal.

Another preferred use of the corrosion inhibitors of the present invention is in aqueous acidic solutions or baths which are in contact with metal surfaces. Such acidic solutions include mineral acid solutions made up of sulfuric acid, hydrochloric acid, nitric acid, phosphoric acid and mixtures thereof. These acidic solutions may be used for acid-pickling baths for the surface cleaning of metals or in similar products. The preferred amount of this corrosion inhibitor in such acid solutions is preferably at least 0.005% by weight of the solution; more preferably, from about 0.01% to about 1% by weight of the bath.

Still another preferred use of the instant corrosion-inhibiting compounds is in hydraulic fluids such as hydraulic brake systems, hydraulic steering mechanisms, hydraulic transmission and the like. Generally, the hydraulic fluids which are already known in the art are usually comprised of a lubricant or base fluid, a diluent portion, and an inhibitor portion. The lubricant or base fluid and the diluent are usually comprised of a wide variety of alcohols, alcohol ethers or a mixture of both. The inhibitor portion normally contains antioxidants and buffers besides corrosion inhibitors. An exemplary list of base fluids, diluents and various additives such as antioxidants, alkaline buffers, rubber swell adjusters and the like are shown in U.S. Pat. No. 3,629,111, which issued to Cramer on Dec. 21, 1971, and in "*Introduction to Hydraulic Fluids*" by Roger E. Hatton, Reinhold Publishing Corporation, 1962. Both of these are incorporated herein by reference in their entireties.

It is believed that the present inhibitor compounds are especially useful in hydraulic fluids which employ polyoxyethylene glycol as the base fluid. Generally, the effective amount of these inhibitors in most hydraulic fluids may range from about 0.1% by weight to about 5.0% by weight of the total fluid; more preferably, from about 0.5 to about 3.0% by weight of the total fluid.

The compounds of this invention may be used for other corrosion protection applications besides these three preferred applications. In addition, it may be desirable that these corrosion inhibitors be applied with other known corrosion inhibitors.

The following examples further illustrate the present invention. All parts and percentages employed herein are by weight unless otherwise indicated.

EXAMPLE 1

3,5-Dimethylpyrazole [28.8 grams (0.3 moles)], toluene (170 milliliters), and a catalytic quantity of powdered potassium hydroxide (about 0.1 gram) were added to a 500 ml, 3-neck flask provided with a thermometer, magnetic stirrer, dry ice/acetone reflux condenser and a pressure-equalized ethylene oxide addition funnel that was cooled with a dry ice jacket. Provision was made to purge the apparatus with $N_2$ and to keep an $N_2$ blanket on during the run. The reactor was heated to reflux (about 110° C.) and ethylene oxide [32.5 grams (0.74 moles)] was slowly added dropwise over a period of 6 hours. This corresponds to a mole ratio of EO to pyrazole of 2.5. The resulting reddish-orange solution was stripped of toluene and unreacted ethylene oxide on a rotary evaporator, yielding a residue of about 50.5 grams. Gas chromatography of this product shows 4 peaks in the area ratio of 59:34:6:1 and believed to correspond respectively to the 1,2,3, and 4 mole ethylene oxide adducts of 3,5-dimethylpyrazole.

EXAMPLE 2

3,5-Dimethylpyrazole [120 grams (1.25 moles)], toluene (300 milliliters), and powdered potassium hydroxide (6 grams) were added to a stainless steel pressure vessel which was then flushed with $N_2$. Ethylene oxide [210 grams (4.75 moles)] was then pressured with $N_2$ into the reaction vessel at a pressure up to 50 psig and a temperature of 130°-140° C. This corresponds to a mole ratio of EO to pyrazole of 3.8. Addition time was 47 minutes with a post addition time of 85 minutes; the temperature was kept in the desired range by periodic cooling by means of a water-cooled coil in the reactor. Toluene and unreacted ethylene oxide were then removed by stripping on a rotary evaporator using a vacuum pump and heating to 74° C. The residue weighed 307 grams, a recovery of 91.3% based on the weight of ethylene oxide and 3,5-dimethylpyrazole added. The elemental analysis of this product was:

|  | C | H | N |
|---|---|---|---|
| Found, % by weight | 57.07 | 8.16 | 10.91 |

-continued

|  | C | H | N |
|---|---|---|---|
| Theory for DMP . 3.8 EO, % | 57.45 | 8.43 | 10.64 |

EXAMPLE 3

Example 2 was repeated, except that a higher ratio of ethylene oxide to 3,5-dimethylpyrazole was used to give a longer polyether chain on the pyrazole ring. 3,5-Dimethylpyrazole [96 grams (1 mole)], toluene (305 grams) and powdered potassium hydroxide (4.8 grams) were charged to the reactor and ethylene oxide [220 grams (5 moles)] was then pressured in, corresponding to an EO to pyrazole mole ratio of 5. After vacuum stripping of toluene and unreacted ethylene oxide, if any, 317 grams of a clear, reddish-orange product remained, representing 98.9% of the starting reactants and catalyst. The elemental analysis of this product was:

|  | C | H | N |
|---|---|---|---|
| Found, % by weight | 56.63 | 8.71 | 8.69 |
| Theory for DMP . 5 EO, % | 56.96 | 8.86 | 8.86 |

EXAMPLE 4

Example 3 was repeated, except with an ethylene oxide to 3,5-dimethylpyrazole molar ratio of 10:1. Analysis of the resulting product was:

|  | C | H | N |
|---|---|---|---|
| Found, % by weight | 55.67 | 8.82 | 4.98 |
| Theory for DMP . 10 EO, % | 55.97 | 8.96 | 5.22 |

EXAMPLE 5

The apparatus and procedure of Example 1 was used to react propylene oxide with 3,5-dimethylpyrazole in a ratio of 2:1, respectively. Analysis of the resulting product was:

|  | C | H | N |
|---|---|---|---|
| Found, % by weight | 60.40 | 8.99 | 16.48 |
| Theory for DMP . 2 PO, % | 62.33 | 9.16 | 17.43 |

Gas chromatographic analysis of this product shows two peaks, presumed to be 85% DMP.1 PO and 15% DMP.2 PO.

EXAMPLE 6

The apparatus and procedure of Example 2 was repeated, except using a molar ratio of propylene oxide to 3,5-dimethylpyrazole of 5:1. The analysis of the resulting product was:

|  | C | H | N |
|---|---|---|---|
| Found, % by weight | 60.73 | 10.01 | 7.30 |
| Theory for DMP . 5 PO, % | 60.96 | 10.16 | 7.49 |

EXAMPLE 7

The apparatus and procedure of Example 2 was repeated, except using a molar ratio of propylene oxide to 3,5-dimethylpyrazole of 10:1. 403 Grams of final product were recovered, representing about 97% of the reactants fed.

EXAMPLE 8

The compounds prepared according to the methods of Examples 4, 6 and 7, above, were tested as corrosion inhibitors in glycol antifreezes according to test method ANSI/ASTM D 1384-70 (Reapproved 1975), "Corrosion Test For Engine Coolants In Glassware". These tests showed that these ethylene oxide and propylene oxide adducts of 3,5-dimethylpyrazole had excellent corrosion-inhibiting properties. The results of these tests are given in Table I, below.

In carrying out this test method D-1384, several antifreeze solutions (each 750 ml) were formed which contained ethylene glycol (250 ml), corrosive water (500 ml), a potassium phosphate buffer [$K_2HPO_4$, (7.5–8 g)] and one of the compounds of Examples 4, 6 and 7 [about 192 grams of each with none for the blank test]. These solutions were placed in 1000 ml beakers. A bundle of six different metal coupons (each coupon having already been weighed) was placed in the beaker and covered by the solution. These beakers were kept at 190° F. for 336 hours, during which time the solutions were aerated. At the end of this time period, the bundles of coupons were removed from the beaker, disassembled, cleaned, reweighed, and the weight change was determined. The weight change per square centimeter of each coupon was determined and is shown in Table I. As can be seen, the weight change with these inhibitors present was much less than the blank test, indicating the excellent protection provided by these compounds.

TABLE I

| Metal | Weight Change (in mg/cm$^2$) | | | |
|---|---|---|---|---|
|  | Blank | DMP . 10 EO | DMP . 5 PO | DMP . 10 PO |
| Copper | 32.7 | 0.46 | 2.36 | 1.49 |
| Solder | 33.9 | 0.22 | 0.38 | 0.36 |
| Brass | 33.2 | 0.26 | 0.23 | 0.45 |
| Steel | 51.8 | 0.07 | 0.05 | 0.05 |
| Cast Iron | 42.5 | +0.08 | +0.07 | 0.03 |
| Aluminum | 3.2 | +0.05 | 0.01 | 0.01 |

EXAMPLE 9

The compounds of Examples 2–7 were further tested as corrosion inhibitors in aqueous acidic solutions according to the linear polarization method described in ASTM test method G5-72. The results of this test are given below in Table II.

By this method, the effectiveness of these compounds as corrosion inhibitors was rated by, first, determining the linear polarization of a mild steel sammple in an uninhibited 1.0 N $H_2SO_4$ solution, and second, in the same 1.0 N $H_2SO_4$ solution after one of the compounds of Examples 2–7 was added (the amount of each compound added was equivalent to 0.25% by weight of the solution). From these linear polarization measurements, the % protection afforded by each inhibitor in this acid solution was determined by the following formula:

$$\% \text{ Protection} = \frac{LP_u - LP_i}{LP_u} \times 100$$

wherein $LP_u$ is the linear polarization of the uninhibited sample and $LP_i$ is the linear polarization of the sample placed in the acid solution containing the inhibitor compound.

As can been seen from Table II, the various ethylene oxide (EO) and propylene oxide (PO) adducts of 3,5-dimethylpyrazole (DMP) are much better than 3,5-dimethylpyrazole by itself.

TABLE II

| Example | Compound | % Protection in 1.0 NH$_2$SO$_4$ |
|---|---|---|
| 2 | DMP . 4 EO | 28.9 |
| 3 | DMP . 5 EO | 88.6 |
| 4 | DMP . 10 EO | 90.1 |
| 5 | DMP . 2 PO | 37.0 |
| 6 | DMP . 5 PO | 95.0 |
| 7 | DMP . 10 PO | 97.2 |
| Comparison 1 | DMP | 8.7 |

EXAMPLE 10

The compound (DMP.10 PO) prepared in Example 7, above, was tested as a corrosion inhibitor in a polyglycol-based hydraulic fluid according to the test method set forth in SAE-J1703f. This poly-glycol-based fluid with the inhibitor included had the following formula:

75.8% Triethyleneglycol monomethylether[1]
20.0% Polypropyleneglycol (molecular weight 1000)[2]
3.0% Polyethylene Glycol (molecular weight 300)[3]
0.2% Bis Phenol-A[4]
0.2% Borax[5]
0.2% Boric Acid[6]
0.2% Trimethylolpropane[7]
0.4% DMP.10 PO

[1] Poly-Solv ® TM manufactured by the Olin Corp. of Stamford, Connecticut.
[2] Poly-G ® 20-112 also manufactured by Olin Corp.
[3] Poly-G ® 300 also manufactured by Olin Corp.
[4,5,6,7] Buffers and antioxidants.

After this hydraulic fluid formulation is made, a bundle of six different metal coupons (previously weighed) were placed in a test jar containing the fluid. All of the coupons were fully covered by the solution. After running the test at 100° C. for 5 days, the coupons were removed, washed, dried, and weighed. The weight change per square centimeter of each coupon was then determined. The results of this corrosion test in the hydraulic fluid containing the DMP.10 PO inhibitor vs. the same uninhibited hydraulic fluid are given in Table III. As can be seen, the hydraulic fluid containing the inhibitor had a smaller weight change for some metals and, thus, offered protection against corrosion.

TABLE III

| | Weight Change of Coupons (in mg/cm$^2$) | |
|---|---|---|
| Metal Coupon | For Unihibited Fluid | For Fluid with DMP . 10 PO |
| Copper | 0.67 | 0.40 |
| Brass | 0.69 | 0.45 |
| Cast Iron | +0.11 | +0.21 |
| Aluminum | +0.01 | 0.005 |
| Steel | +0.35 | 0.02 |
| Tin | +0.01 | 0.03 |

What is claimed is:

1. A poly(oxyalkylated) pyrazole having the formula:

$$R-C\underset{N-N}{\overset{CH}{=}}C-R' \atop (CH_2-CHO)_{\overline{n}}H \atop R''$$

wherein R and R' are independently selected from lower alkyl groups having from 1 to 4 carbon atoms; each R'' is individually selected from hydrogen and methyl; and n is from 2 to about 20.

2. The compound of claim 1 wherein R and R' are both methyl.

3. The compound of claim 1 wherein each R'' is hydrogen.

4. The compound of claim 1 wherein each R'' is methyl.

5. The compound of claim 4 wherein n is from about 5 to about 20.

6. The compound of claim 1 wherein R and R' are both methyl and n is from about 5 to about 20.

7. A corrosion inhibited antifreeze composition comprising a water-soluble liquid alcohol freezing point depressant and an effective corrosion-inhibiting amount of a poly(oxyalkylated) pyrazole having a formula:

$$R-C\underset{N-N}{\overset{CH}{=}}C-R' \atop (CH_2-CHO)_{\overline{n}}H \atop R''$$

wherein R and R' are independently selected from lower alkyl groups having from 1 to 4 carbon atoms; each R'' is individually selected from hydrogen and methyl; and n is from 2 to about 20.

8. The antifreeze composition of claim 7 wherein said liquid alcohol freezing point depressant is ethylene glycol.

9. The antifreeze composition of claim 7 wherein R and R' are both methyl and n is from about 5 to about 20.

10. A process for inhibiting the corrosion of metals which come in contact with an antifreeze composition, which comprises contacting the surface of the metal to be inhibited against corrosion with the antifreeze composition of claim 7.

11. The process of claim 10 wherein the liquid alcohol freezing point depressant is ethylene glycol.

12. An acid metal treating bath comprising an acid and an effective corrosion-inhibiting amount of a poly(oxyalkylated) pyrazole having a formula:

$$R-C\underset{N-N}{\overset{CH}{=}}C-R' \atop (CH_2-CHO)_{\overline{n}}H \atop R''$$

wherein R and R' are independently selected from lower alkyl groups having from 1 to 4 carbon atoms; each R'' is individually selected from hydrogen and methyl; and n is from 2 to about 20.

13. The acid bath of claim 12 wherein the acid comprises sulfuric acid, hydrochloric acid, nitric acid, phosphoric acid and mixtures thereof.

14. The acid bath of claim 12 wherein R and R' are both methyl and n is from about 5 to about 20.

15. A process for inhibiting the corrosion of metals which come into contact with an acid solution, which comprises contacting the surface of the metal to be inhibited against corrosion with the corrosion-inhibiting acid metal treating bath of claim 12.

16. The process of claim 15 wherein the acid in said acid bath comprises sulfuric acid, hydrochloric acid, nitric acid, phosphoric acid and mixtures thereof.

17. A corrosion-inhibited hydraulic fluid composition comprising a base fluid component and an effective corrosion-inhibiting amount of a poly(oxyalkylated) pyrazole having the formula:

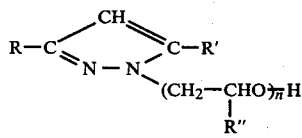

wherein R and R' are independently selected from lower alkyl groups having from 1 to 4 carbon atoms; each R'' is individually selected from hydrogen and methyl; and n is from 2 to about 20.

18. The hydraulic fluid composition of claim 17 wherein the base fluid component comprises polyoxyethylene glycol.

19. The hydraulic fluid composition of claim 17 wherein R and R' are both methyl and n is from about 5 to about 20.

20. A process for inhibiting the corrosion of metals which come in contact with a hydraulic fluid composition, which comprises contacting the surface of the metal to be inhibited against corrosion with the hydraulic fluid composition of claim 13.

21. The process of claim 20 wherein the base fluid component comprises polyoxyethylene glycol.

22. A process for inhibiting corrosion of metal surfaces caused by corrosive aqueous solutions, which comprises
contacting said metal with an effective corrosion-inhibiting amount of a poly(oxyalkylated) pyrazole of the formula

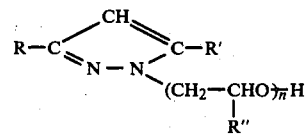

wherein R and R' are independently selected from lower alkyl groups having 1 to 4 carbon atoms; each R'' is individually selected from hydrogen and methyl; and n is from 2 to about 20.

23. The process of claim 22 wherein R and R' are both methyl.

24. The process of claim 22 wherein each R'' is hydrogen.

25. The process of claim 22 wherein each R'' is methyl.

26. The process of claim 25 wherein n is from about 5 to about 20.

27. The process of claim 22 wherein R and R' are both methyl and n is from about 5 to about 20.

* * * * *